(12) United States Patent
Nikolskaya

(10) Patent No.: US 6,840,084 B2
(45) Date of Patent: Jan. 11, 2005

(54) GAS MONITORING SYSTEM AND METHOD

(76) Inventor: Elena Nikolskaya, Vitebsky pr., 63, Apartment 142, St. Petersburg (RU), 196 233

( * ) Notice: Subject to any disclaimer, the term of this patent is extended or adjusted under 35 U.S.C. 154(b) by 31 days.

(21) Appl. No.: 10/202,590

(22) Filed: Jul. 24, 2002

(65) Prior Publication Data
US 2004/0016288 A1 Jan. 29, 2004

(51) Int. Cl.[7] .......................... G01N 9/00; G01N 27/26; G08B 17/00
(52) U.S. Cl. ....................... 73/23.2; 73/31.05; 340/632; 436/124
(58) Field of Search ............................... 73/23.2, 31.05; 340/632; 436/124; 205/779.5; 204/412; 422/56

(56) References Cited

U.S. PATENT DOCUMENTS

| | | | | |
|---|---|---|---|---|
| 4,127,386 A | | 11/1978 | Stahl et al. | |
| 4,141,800 A | * | 2/1979 | Breuer et al. | 205/779.5 |
| 4,205,043 A | * | 5/1980 | Esch et al. | 422/56 |
| 4,256,543 A | * | 3/1981 | Petersen et al. | 205/779.5 |
| 4,571,292 A | * | 2/1986 | Liu et al. | 204/412 |
| 4,633,704 A | * | 1/1987 | Tantram et al. | 73/31.05 |
| 6,252,510 B1 | * | 6/2001 | Dungan | 340/632 |
| 6,284,545 B1 | | 9/2001 | Warburton et al. | |
| 6,548,024 B1 | * | 4/2003 | Doncaster et al. | 422/88 |
| 6,670,887 B2 | * | 12/2003 | Dungan | 340/632 |

* cited by examiner

Primary Examiner—Hezron Williams
Assistant Examiner—Jacques M. Saint-Surin
(74) Attorney, Agent, or Firm—Yongzhi Yang; Marianne Fuierer; Steven J. Hultquist

(57) ABSTRACT

An apparatus and method for monitoring a source gas for detection of phosgene and/or chlorine dioxide therein, in which the source gas is filtered for removal of hydrogen sulfide and/or chlorine and/or hydrogen chloride prior to monitoring of the source gas by a gas sensor specific for phosgene or chlorine dioxide detection. The filter includes a support having $Ag_2O$ thereon, and when the source gas contains chlorine dioxide, chlorine also is present in the source gas prior to its filtration.

25 Claims, 1 Drawing Sheet

GAS MONITORING SYSTEM AND METHOD

BACKGROUND OF THE INVENTION

1. Field of the Invention

The present invention relates generally to a gas monitoring system, and more specifically to a system including a filter and a gas sensor, in which the filter removes hydrogen sulfide and/or chlorine and/or hydrogen chloride from a source gas that is provided to the gas sensor for sensing of other component(s) therein.

2. Description of the Related Art

Gas sensors are used in many applications for the detection of hazardous gas component(s) in a gas stream or gas environment. These hazardous gas component(s), hereafter referred to as "target gas," may be of widely varying types. Their hazardous character may derive from their toxicity to humans, pyrophoricity, explosive character, flammability, deactivating character as regards materials used for abatement or reclamation of other components in the gas mixture.

In many applications, the gas sensor is not strictly selective for the target gas, and the other component(s) of the gas being monitored may interefere with or preclude the proper operation of the gas sensor. For example, gas component(s) other than the target gas can produce the same signal or response by the sensor, so that the concentration of the target gas in the gas stream or environment being monitored is misattributed by the gas sensor.

Such misattribution of the concentration of the target gas can have severe consequences for the process operation or action that is conducted based on the sensed concentration of the target gas. For example, vital steps of an industrial process may be curtailed or unduly prolonged due to the incorrect sensing of target gas, with consequent adverse effect on the process economics or safety. Action may be taken based on the misattributed target gas sensing that is wasteful or even superfluous.

Such undesirable behavior of the gas sensor can be prevented by the use of gas filters that remove from the gas being monitored by the gas sensor, those component(s) that would otherwise interfere with the accurate sensing of the target gas by the gas sensor.

The present invention relates to gas filters for such purpose, and to gas monitoring systems that comprise such filters.

Phosgene ($COCl_2$) is a chemical of major industrial importance. The annual production worldwide is more than 1 million tons, 90% of which is used in the manufacture of isocyanates and polyurethane and polycarbonate resins. Phosgene is also extensively used as a synthetic reagent in a wide variety of organic chemical processes, e.g., the synthesis of numerous chloride compounds.

Phosgene also is a hazardous chemical compound, since it readily decomposes in the presence of water to yield HCl and $CO_2$. Phosgene also is highly adsorbable, even by such chemically inert materials as polytetrafluoroethylene (PTFE), in addition to being highly toxic, irritating and corrosive in character. Inhalation of phosgene can cause fatal respiratory damage. Due to its colorless, odorless character, phosgene is a gas that requires, sensitive, accurate and reliable monitoring in gas streams or environments in which it is or may be present.

Due to its hazardous character, the maximum workplace concentration (MWC) of phosgene during a 40 hour week in a workplace environment is 0.1 parts per million by volume (ppmv).

Chlorine dioxide ($ClO_2$) is another chlorine-containing hazardous gas, whose MWC value also is 0.1 ppmv. $ClO_2$ is manufactured on a large scale, as is used as a substitute for chlorine or ozone in many industrial applications. Its uses include biocidal applications (e.g., in the pulp and paper industry), disinfection applications (in municipal water treatment, treatment of medical waste, and food applications), circuit board cleaning in the electronics industry, treatment of sulfides in the petroleum industry, and bleaching applications in the textile industry, to name a few. An advantage of using $ClO_2$ is that it does not directly form halogenated byproducts, as is the case when chlorine is employed. Like chlorine, $ClO_2$ is a very strong oxidant. $ClO_2$ also has the advantage that it does not form dioxins.

$ClO_2$, however, is not stable, and it therefore is typically produced at the point of use (POU) location, in the amount that is required. Chlorine dioxide is a highly reactive gas, readily entering into disproportion reactions, decomposing to HCl and $HClO_3$ in the presence of water, or to $ClO_3$ and $H_2O$ in alkaline solution. $ClO_2$ is able to react as an oxidative or a reductive agent. It can be oxidized by strong oxidants such as potassium permanganate but in many instances reacts as an oxidant itself. Chlorine dioxide is highly adsorbable, e.g., by activated carbon. Due to its high toxicity, it is necessary to monitor chlorine dioxide in an accurate, sensitive and reliable manner.

Electrochemical sensors are widely used for measuring the concentration of toxic gases (see, for example, Advances in Electrochemistry and Electrochemical Engineering, Volume 10 (J. Wiley & Sons, 1976). A potential disadvantage of electrochemical sensors is their cross-sensitivity to other hazardous gases that may be present in the stream or environment being monitored for a target gas.

Considering the aforementioned gases $COCl_2$ and $ClO_2$ as target gas species, which are desirably monitored in environments and/or process streams containing same, it is to be noted that the presence of $COCl_2$ and/or $ClO_2$ gas in many applications is accompanied by the presence of hydrogen sulfide and/or chlorine and/or HCl. The latter gases are less toxic than phosgene or chlorine dioxide, as shown by their MWC values. Whereas $COCl_2$ and $ClO_2$ each have a MWC value of 0.1 ppmv, the MWC value of $Cl_2$ is 1.0 ppmv, the MWC value of HCl is 5.0 ppmv and the MWC value of $H_2S$ is 10.0 ppmv.

$H_2S$ is easily oxidized in the following reaction:

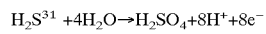
$$H_2S^{31} + 4H_2O \rightarrow H_2SO_4 + 8H^+ + 8e^-$$

and chlorine is a strong oxidant:

$$Cl_2 + 2e^- \rightarrow 2Cl^- \quad Eo = 1.36 \text{ volts}$$

In electrochemical sensors for $COCl_2$, phosgene produces an anode current. In electrochemical sensors for chlorine dioxide, the $ClO_2$ gas produces a cathode current by the following reduction reaction

$$ClO_2 + 4H^+ + 5e^- \rightarrow 2H_2O + Cl^- \quad E_o = 1.27 \text{ volts}$$

In such sensors for phosgene and chlorine dioxide, the sensor response to $H_2S$ has the same polarity as the sensor response to phosgene, and the opposite polarity to the response of the sensor to chlorine dioxide.

Thus, the presence of hydrogen sulfide in an air mixture with phosgene will produce a false higher response of the sensor to phosgene, and the presence of hydrogen sulfide in an air mixture with chlorine dioxide will produce a false lower response of the sensor to chlorine dioxide, even when the hydrogen sulfide in the respective air mixtures is at a level below the MWC value.

Correspondingly, in such sensors for phosgene and chlorine dioxide, the sensor response to chlorine has the opposite polarity to the response of the sensor to $COCl_2$ and the same polarity as the response of the sensor to $ClO_2$.

Thus, the presence of chlorine in an air mixture with phosgene will produce a false lower response of the sensor to phosgene, and the presence of chlorine in an air mixture with chlorine dioxide will produce a false higher response of the sensor to chlorine dioxide, even when the chlorine in the respective air mixtures is at a level below the MWC value.

When both hydrogen sulfide and chlorine are present with the target gas in a three-component gas mixture, the phosgene sensor or chlorine dioxide sensor will show a superpositional response, i.e., an algebraic summation of the responses of the sensor to each gas component.

Hydrogen chloride (HCl) poisons $COCl_2$ sensors, which typically use gold working electrodes. It is thought that the Cl− anion forms complexes with the gold electrode thereby preventing accurate determination of $ClO_2$ concentration. As one example, 10.0 ppmv HCl distorts a $ClO_2$ sensor signal by between about 150 and 300 nA.

Hydrogen sulfide, chlorine and hydrogen chloride are also interferent gas components for other electrochemical gas sensors, e.g., those employed for monitoring of target gas species such as sulfur dioxide, nitrogen dioxide, hydrogen, hydrogen chloride and ammonia.

The use of chemically selective filters is known in the art, wherein the filter effects removal of the interferent gas species from the gas being monitored, so that the filtered gas subsequently exposed to the gas sensor produces a concentration sensing for the target gas that is unaffected by the presence of the interferent gas species, and thereby accurate for the target gas. For example, hydrogen sulfide filters are described in Warburton et al. U.S. Pat. No. 6,284,545 and are otherwise known, which operate by oxidation or adsorption of the hydrogen sulfide component of the gas mixture containing same, using filters employing manganese dioxide, potassium permanganate, activated carbon, activated carbon with manganese dioxide, etc. Such filters are effective in removing hydrogen sulfide as well as chlorine, but at the same time they also remove phosgene and chlorine dioxide with very high effectiveness. In consequence, these filters produce a filtered gas that is misrepresentative of the concentration of phosgene and chlorine dioxide in the original source gas (i.e., prior to filtering), producing false lower sensed concentrations of the target gas. Such false low reading of the target gas concentration by the gas sensor thus creates a situation of potential danger to personnel in the vicinity of the source gas as well as inadequate treatment or processing of gas due to the false lower sensed concentration of the target gas.

The art therefore is in need of a gas sensing system for monitoring concentration of phosgene and chlorine dioxide in instances where the source gas being monitored contains hydrogen sulfide and/or chlorine, and/or hydrogen chloride.

SUMMARY OF THE INVENTION

The present invention relates generally to an apparatus and method for monitoring a source gas for detection of phosgene and/or chlorine dioxide therein, in which the source gas is filtered for removal of hydrogen sulfide and/or chlorine, and/or hydrogen chloride prior to monitoring of the source gas by a gas sensor specific for phosgene and/or chlorine dioxide detection.

In one aspect, the invention relates to a monitored gas system, comprising:

a source gas;

a gas sensor constructed and arranged to monitor the source gas for detection of at least one of, phosgene and chlorine dioxide therein; and a filter for removal of at least one of, hydrogen sulfide, chlorine, and hydrogen chloride, from the source gas prior to its monitoring by the gas sensor, said filter comprising a support having $Ag_2O$ thereon; wherein, when said source gas contains chlorine dioxide, chlorine is present in said source gas prior to filtration of said source gas by said filter.

Another aspect of the invention relates to a gas monitoring system for a source gas, comprising:

a gas sensor constructed and arranged to detect phosgene in said source gas; and a filter for removal of at least one of, hydrogen sulfide, chlorine and hydrogen chloride from the source gas prior to its exposure to the gas sensor, said filter comprising a support impregnated with $Ag_2O$.

A still further aspect of the invention relates to a method of monitoring a source gas for at least one of phosgene and chlorine dioxide therein, comprising:

filtering the source gas to remove at least one of hydrogen sulfide, chlorine and hydrogen chloride therefrom to produce a filtered source gas, by contacting the source gas with a filter comprising a support having $Ag_2O$ thereon; and exposing the filtered source gas to a gas sensor constructed and arranged to detect at least one of, phosgene and chlorine dioxide therein; wherein when said source gas contains chlorine dioxide, chlorine is present in said source gas prior to filtering thereof.

Other aspects, features and embodiments of the invention will be more fully apparent from the ensuing disclosure and appended claims.

DETAILED DESCRIPTION OF THE INVENTION, AND PREFERRED EMBODIMENTS THEREOF

Figure 1:
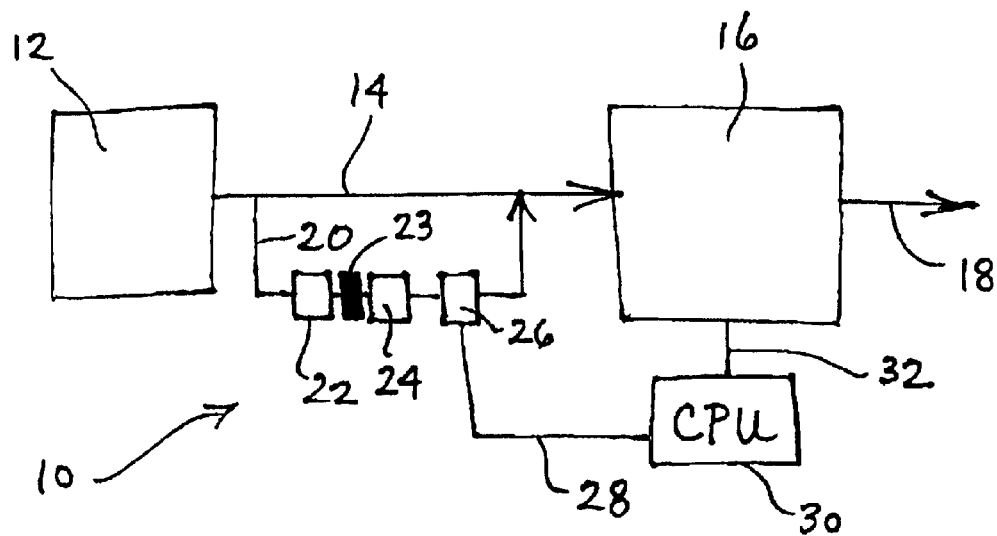
FIG. 1 is a schematic representation of a process system employing a gas sensor and associated gas filter according to the present invention, in an illustrative embodiment thereof.

The present invention provides a gas sensing system useful for monitoring phosgene and/or chlorine dioxide, as a target gas, in a source gas containing at least one of, hydrogen sulfide, chlorine and hydrogen chloride in mixture with such target gas. The gas sensing system utilizes a gas filter that is highly selective for hydrogen sulfide and/or chlorine and/or hydrogen chloride in such source gas, and is substantially non-interactive with the target gas species. When the source gas is an air mixture containing the target gas and at least one of, hydrogen sulfide, chlorine and hydrogen chloride, the gas filter is effective even in the presence of moisture, over a wide range of humidity of the source gas.

The gas filter in the gas sensing system of the invention in one embodiment includes an inert high porosity support with finely divided silver (I) oxide in the support. When contacted with the source gas containing phosgene and/or chlorine dioxide, in combination with at least one of hydrogen sulfide ($H_2S$), chlorine ($Cl_2$), and hydrogen chloride (HCl), the concentration of at least one of $H_2S$, $Cl_2$ and HCl is reduced from the source gas to yield a sensing gas mixture whose concentration of the target gas species is substantially unchanged from the source gas.

The gas filter in accordance with the invention includes a high porosity support for penetration of the source gas, and an active agent on the support. The gas filter has a high removal capacity for the interferent hydrogen sulfide and/or chlorine and/or hydrogen chloride species present in the source gas, and is effective to remove substantially all of the interferent gas species from the source gas. The filter is substantially non-interactive with the target gas species in the source gas, whereby the concentration of the target species in the source gas after filtration is substantially equal to the concentration of the target gas species in the source gas prior to filtration treatment of the source gas to provide the sensing gas mixture.

The active agent in the gas filter of the invention comprises a silver (I) compound which forms insoluble compounds with both sulfide and chlorine ions, and is substantially non-reactive with phosgene and with chlorine dioxide, whereby an associated phosgene sensor or associated chlorine dioxide sensor provides an accurate and reproducible sensing of the respective target gas species. Table 1 below sets out illustrative silver (I) compounds and their solubility product coefficient values, $K_{sp}$.

TABLE 1

SOLUBILITY PRODUCT COEFFICIENT

| SALT | K sp |
|------|------|
| $Ag_2S$ | $1 \times 10^{-49}$ |
| AgCl | $1.6 \times 10^{-10}$ |
| $Ag_2O$ | $2.0 \times 10^{-8}$ |

The active agent and the support of the gas filter of the invention are preferably selected to provide a support with suitably high surface for extended lifetime operation in conjunction with the gas sensor, so that interferent species are removed from the source gas for sensing by the gas sensor, during the entire operating life of the sensor. The active agent and the support of the gas filter are also preferably selected to provide high stability of the filter during the gas monitoring operation, e.g., over a wide range of relative humidity when the source gas comprises ambient air in mixture with the target gas and the interferent gases, and the ambient air contains moisture (a non-zero relative humidity). The silver compound and the support are desirably selected to provide a high and enduring level of association (adhesion) of the silver compound to the support. In one preferred aspect of the invention, the silver compound is hydrophobic in character, e.g., a hydrophobic silver salt.

The silver compound is suitably applied to the support by impregnation of the silver compound from a solution of the compound, with which the support is contacted, followed by drying of the contacted support to evaporate the solvent and yield the silver compound-impregnated support. When the silver compound is hydrophilic in nature, the impregnation solution may be an aqueous solution of the silver compound, e.g., a silver salt, but the resulting gas filter should be used in services where the source gas is anhydrous (moisture-free) since the presence of water in the source gas in such case will result in the $H_2S/Cl_2/HCl$ removal capability of the filter varying with the relative humidity of the source gas.

A preferred silver compound in the gas filter of the invention is $Ag_2O$, which is water-insoluble and hydrophobic, and therefore stable over a wide relative humidity range for filtering hydrogen sulfide, chlorine and hydrogen chloride from source gas that contains moisture.

As shown in Table 1, the coefficient of the solubility product ($K_{sp}$) for $Ag_2O$ is far higher than for $Ag_2S$ (by about 40 orders of magnitude) and for AgCl (by 2 orders of magnitude). The removal of hydrogen sulfide, chlorine and hydrogen chloride with an $Ag_2O$-based filter is highly effective, while at the same time the silver oxide active agent does not adsorb or otherwise interact with the target gas ($COCl_2$ or $ClO_2$). Further, the reaction products of the reaction of $Ag_2O$ with hydrogen sulfide, chlorine and hydrogen chloride are non-reactive with the target gas, do not clog the filter, and include reaction product species (e.g., AgCl) that are also useful for hydrogen sulfide removal. Silver chloride is reactive with hydrogen sulfide (see Table 1 hereinabove, showing a $K_{sp}$ difference for $Ag_2S$ and AgCl of about 40 orders of magnitude). The filter thus effects the following reactions:

$Ag_2O+H_2S=Ag_2S+H_2O$

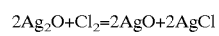

$2Ag_2O+Cl_2=2AgO+2AgCl$

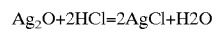

$Ag_2O+2HCl=2AgCl+H2O$

The support for the filter of the present invention in a preferred embodiment is a needled glass mat without binder. A particularly preferred binderless needled glass mat for such purpose is commercially available as ecoMat Type G 300 (Johns Manville Sales GmbH), which provides high efficacy in use of $Ag_2O$ as the active removal agent, and is completely inert to both $COCl_2$ and $ClO_2$, other components of the gas mixture and the electrolyte. The mat is a highly porous glass material with a square meter weight of more than 300 grams/m², providing a highly gas-penetrable structure for the target gas.

In a preferred embodiment using the binderless needled glass mat, the active agent is $Ag_2O$ in the form of a finely divided powder spread on the high surface area needles in the mat, to provide a thin layer of silver oxide fine particles. The thin layer of silver oxide fine particles has very good adhesion to the needled glass mat, providing a high filtering capacity for hydrogen sulfide, hydrogen chloride and chlorine. Adhesion to the needled glass mat of the removal reaction products ($Ag_2S$ and AgCl) is also high.

A particularly complex issue faced in the development of the filter of the present invention relates to the ratio of the MWC of the gases present in the source gas to be analyzed.

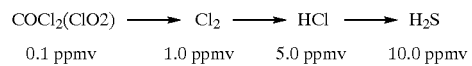

| $COCl_2(ClO2)$ | $Cl_2$ | HCl | $H_2S$ |
|---|---|---|---|
| 0.1 ppmv | 1.0 ppmv | 5.0 ppmv | 10.0 ppmv |

The objective is to reliably measure low concentration (<0.1 ppmv) of the target gas (phosgene or chlorine dioxide) in presence of harmful gases which concentrations could be, for example, about one order ($Cl_2$), more than 1.5 order (HCl), or even two orders ($H_2S$) of magnitude higher. The present invention achieves such objective by providing high gas sensor sensitivity to the target as, high kinetic rates for removal of hydrogen sulfide, chlorine and hydrogen chloride from the source gas, and high filter capacitance for hydrogen sulfide, chlorine and hydrogen chloride.

The phosgene or chlorine dioxide sensor in the practice of the present invention is of any suitable type, such as an electrochemical sensor including an assembly of working, reference and counter electrodes or working and counter electrodes, wherein the successive electrodes are separated from one another by separator elements, and disposed in a housing containing an electrolyte.

The hydrogen sulfide/chlorine/hydrogen chloride filter of the invention is advantageously deployed in proximity to the sensor, and in a preferred aspect, the $H_2S/Cl_2/HCl$ filter is beneficially integrated with the electrochemical sensor for phosgene or chlorine dioxide monitoring of the source gas. The interferent species filter for $H_2S/Cl_2/HCl$ removal may be deployed downstream of a dust filter, to remove particulates that could otherwise interfere with the proper operation of the interferent species filter and the gas sensor. In such arrangement, the source gas flows sequentially through the dust filter, interferent species filter and the electrochemical sensor. The dust filter may be disposed in a unitary assembly of the interferent species filter and the gas sensor, to provide an integrated gas sensing assembly, as hereinafter more fully described.

The dust filter, when employed, should be appropriately designed with respect to the flow impedance characteristics of such filter, since the dust filter may serve to alter the sensitivity of the gas sensor. The porosity of the dust filter therefore is a design parameter and should be appropriately selected to provide a desired sensitivity in the gas sensor, since increasing the porosity of the dust filter increases the sensitivity of the $COCl_2$ or $ClO_2$ sensor. Additionally, the interferent species filter should be designed to avoid uptake of any target gas species, and therefore such filter is desirably formed of materials of construction, as to the housing and filtering medium, and associated flow circuitry thereof. Such dust filter/interferent species filter arrangement is advantageously optimized with respect to dust filter porosity, thickness of the support in the interferent species filter, and quantity of active agent (e.g., $Ag_2O$) on the support in the interferent species filter.

$Ag_2O$ as a preferred active agent for the interferent species filter forms insoluble salts to bind sulfide anion without hazardous side reaction products, providing a stable selective filter with high capacitance for hydrogen sulfide. Concurrently, the difference between $K_{sp}$ for $Ag_2O$ and AgCl enables the efficient removal of chlorine and hydrogen chloride from the source gas, and provides a means for achieving high sensitivity and selectivity for the target gas in source gas mixtures including the target gas, hydrogen sulfide, hydrogen chloride and chlorine.

Referring now to the drawings, FIG. 1 is a schematic representation of a process system employing a gas sensor and associated gas filter according to the present invention, in an illustrative embodiment thereof.

The FIG. 1 process system 10 includes a supply 12 of the source gas. The supply 12 may include a process unit that generates the target gas in mixture with at least one of, hydrogen sulfide, chlorine and hydrogen chloride, as a multicomponent gas mixture. Alternatively, the supply 12 of the source gas may be a gas environment that is subject to ingress or contamination by the target gas in mixture with interferent gas species ($H_2S$ and/or HCl and/or $Cl_2$). The source gas, containing phosgene or chlorine dioxide, in addition to at least one of hydrogen sulfide, chlorine and drogen chloride, flows from supply 12 in line 14 to the abatement processing unit 16 in which the source gas is treated to remove the phosgene or chlorine dioxide therefrom.

A phosgene-depleted, or chlorine dioxide-depleted, stream is discharged from the abatement processing unit 16 in line 18, and may be passed to a further downstream process or final disposition, as required.

A side stream of the source gas from line 14 is flowed in line 20, under the action of motive fluid driver 22, through dust filter 23, interferent species filter 24 and gas sensor 26, being returned to line 14 downstream of gas sensor 26, as shown. The dust filter 23 removes particulates from the source gas, and the interferent species filter 24 removes hydrogen sulfide and/or chlorine and/or hydrogen chloride from the dust-depleted source gas, to provide an interferent-free gas mixture comprising the phosgene or chlorine dioxide component, to the gas sensor 26.

The gas sensor 26 monitors the concentration of the target gas (phosgene or chlorine dioxide) in the side stream and generates a corresponding response signal correlative to the sensed concentration of the target gas species. The response signal is transmitted in signal transmission line 28 to central processing unit (CPU) 30, which in turn generates a corresponding control signal that is transmitted in control signal line 32 to the abatement processing unit 16. The control signal in line 32 may be employed to modulate the gas processing operation in abatement processing unit 16 to abate the target gas species.

For example, if phosgene is the target gas species in the source gas, and such target gas species is abated by chemical reaction thereof with a chemical reagent in the abatement processing unit 16, the amount of the chemical reagent may be modulated in response to the sensed concentration of the phosgene in the source gas, to effect substantially complete removal of the phosgene from the gas stream treated in abatement processing unit 16. In other abatement operations, the process conditions (e.g., temperatures, pressures, flow rates, retention time) in the abatement-rocessing unit 16 may be modulated to effect the desired reduction in the concentration of the target gas species in the effluent stream being treated.

Figure 2:
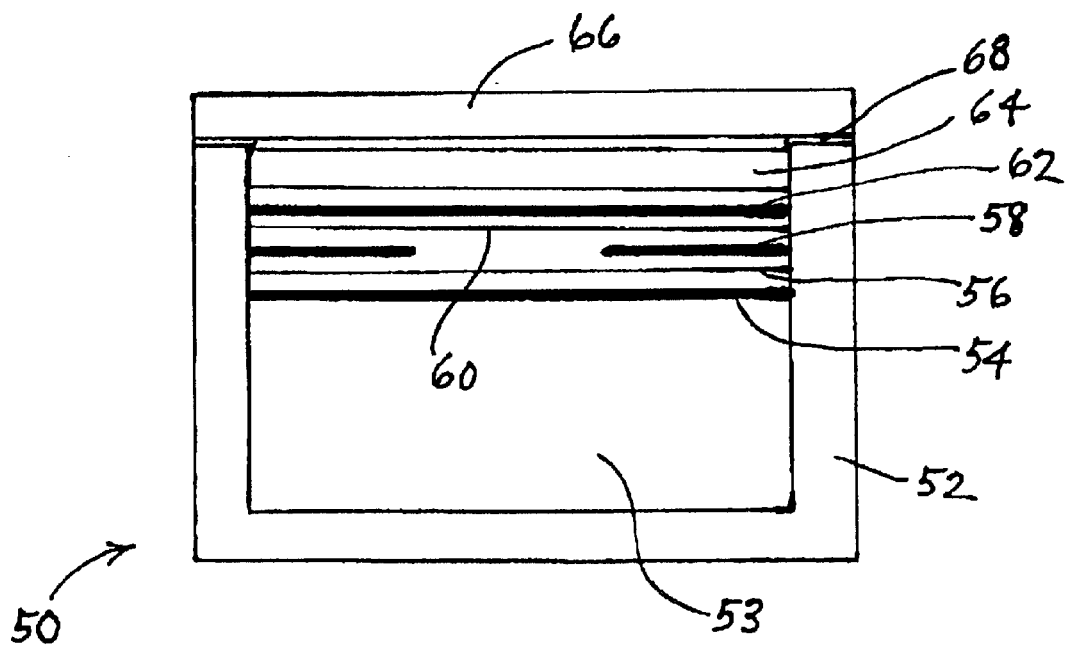
FIG. 2 is a schematic representation of a gas sensor and filter unit according to one embodiment of the invention.

FIG. 2 is a schematic representation of an integrated gas sensor and filter unit 50 according to one embodiment of the invention.

The integrated gas sensor and filter unit 50 comprises a housing 52 formed of a suitable material of construction, e.g., nonporous ceramic, polymer, etc. defining therewithin an interior volume. The interior volume of the housing includes an electrolyte compartment 53 containing a suitable electrolyte, and an electrode assembly including a counter electrode 54, a reference electrode 58 and a working electrode 62, wherein the counter and reference electrodes are separated by separator member 56, and the reference and working electrodes are separated by separator member 60.

Overlying the electrode assembly is an interferent species filter 64 for removing hydrogen sulfide and/or chlorine and/or hydrogen chloride from the source gas flowed therethrough. A dust filter 66 is joined to the housing 52 at the upper end of the housing walls, as shown, being sealed to the top edges of the walls by bond 68. The bond 68 is formed of a suitable adhesive or sealant medium, and joins the dust filter 66 to the housing 52 in a leak-tight manner, so that source gas flowed through the filter enters the interferent species filter 64 and is prevented from bypassing the filtration and sensing elements in the housing interior volume.

It will be recognized that the integrated gas sensor and filter unit 50 is schematically illustrated for ease of description, and does not show the electrical leads to the electrode elements in the housing or other ancillary structure, but based on such description, the integrated gas sensor and filter unit 50 may be readily constructed by those skilled in the art, to effect gas sensing operation that is accurate and reproducible for monitoring of the target gas (phosgene or chlorine dioxide) species in the source gas.

The features and advantages of the invention are more fully shown by the following non-limiting examples.

EXAMPLE 1

An interferent species filter is fabricated from a needled glass mat (ecoMat Type G 300; Johns Manville Sales GmbH). The mat is heated at a temperature of 300° C. in air for 3 hours to clean the surface. Disks having a diameter of 8 mm are punched from the mat, to provide support members each having a mass of from about 13.0 mg to about 17.5 mg (average 15.2 mg±15%).

A quantity of 330 mg of fine silver (I) oxide powder is introduced to a glass vessel, and 1.0 milliliter of acetone and 0.2 milliliter of water are added. The vessel then is closed after a magnetic stirrer element is placed in the powder/solvent mixture, and the vessel contents then are mixed on a magnetic stirrer for 3 minutes to homogenize the suspension, and thereafter the suspension is continually stirred to maintain a homogeneous suspension composition.

Ten of the glass mat disks are placed on an elevated polymer net, comprising a polyethylene net that is disposed on a Petri cap. The suspension of $Ag_2O$ then is pipetted and 5 drops are introduced onto each needled glass disk from the pipette, following which 4–5 drops of pure acetone is introduced from a separate pipette onto each needled glass disk, to spread the fine silver oxide more uniformly throughout the full volume of the needled glass disk.

The disks then are dried on the elevated polymeric net for 30 minutes in ambient air at room temperature in a dark (light-free) environment, following which the disks are heated in an oven at 45° C. for 2 hours.

The impregnated disk then is placed in a sensor cap, and the disk is covered with a high porosity PTFE dust filter, glued at its perimeter to the sensor cap as shown in FIG. 2 hereof.

The foregoing construction in application to a phosgene gas sensor assembly yielded the results shown in Table 2 below.

TABLE 2

| Gas species, concentration in ppmv | Gas sensor without interferent species filter, nA/ppmv | Gas sensor with interferent species filter, nA/ppmv | Interferent species filter capacitance, ppmv h |
|---|---|---|---|
| 0.33 ppm $COCl_2$ | 960 | 710 | — |
| 10 ppm $H_2S$ | 350 | 0 | 60 |
| 1 ppm $Cl_2$ | −1100 | 0 | 2 |
| 1 ppm HCl | 600 | 0 | 0.5 |

A corresponding construction in application to a chlorine dioxide gas sensor assembly yielded the results shown in Table 3 below.

TABLE 3

| Gas species, concentration in ppmv. | Gas sensor without interferent species filter, nA/ppmv | Gas sensor with interferent species filter, nA/ppmv | Interferent species filter capacitance, ppmv h |
|---|---|---|---|
| 1 ppm $ClO_2$ | −990 | −990 | — |
| 10 ppm $H_2S$ | 300 | 0 | 13 |
| 1 ppm $Cl_2$ | −300 | 0 | >1 |
| 10 ppm HCl | 260 | 0 | >10 |

Table 4 below shows the influence of the exposure of the integrated filter/sensor unit to 10 ppmv of $H_2S$, to 1 ppmv $Cl_2$ and 1 ppmv HCl for both phosgene and chlorine dioxide sensors.

TABLE 4

| Sensor type | Sensor response to target gas, nA/ppm | Sensor after exposure to hydrogen sulfide, nA/ppm | Sensor after exposure to chlorine, nA/ppm | Sensor after exposure to hydrogen chloride, nA/ppm |
|---|---|---|---|---|
| $COCl_2$ sensor | 1200 | 940 | | |
| $COCl_2$ sensor | 960 | | 830 | |
| $COCl_2$ sensor | 850 | | | 810 |
| $ClO_2$ sensor | −580 | −620 | | |
| $ClO_2$ sensor | −910 | | −1310 | |
| $ClO_2$ sensor | −600 | | | −580 |

Although the invention has been variously disclosed herein with reference to illustrative embodiments and features, it will be appreciated that the embodiments and features described hereinabove are not intended to limit the invention, and that other variations, modifications and other embodiments will suggest themselves to those of ordinary skill in the art. The invention therefore is to be broadly construed, consistent with the claims hereafter set forth.

What is claimed is:

1. A monitored gas system, comprising:
    a source gas;
    a gas sensor constructed and arranged to monitor the source gas for detection of phosgene and/or chlorine dioxide therein; and
    a filter for removal of hydrogen sulfide and/or chlorine from the source gas prior to its monitoring by the gas sensor, said filter comprising a support having $Ag_2O$ thereon;
    wherein when said source gas contains chlorine dioxide, chlorine is present in said source gas prior to filtration of said source gas by said filter.

2. The monitored gas system of claim 1, wherein the gas sensor is arranged to provide an output signal correlative of the concentration of phosgene and/or chlorine dioxide therein.

3. The monitored gas system of claim 2, further comprising means for treating the source gas subsequent to monitoring thereof by the gas sensor.

4. The monitored gas system of claim 3, wherein said means for treating the source gas are constructed and arranged to at least partially remove phosgene and/or chlorine dioxide from the source gas.

5. The monitored gas system of claim 4, wherein said treating means for at least partial removal of phosgene and/or chlorine dioxide is controlled by or in response to the output signal correlative of the concentration of phosgene and/or chlorine dioxide in the source gas.

6. The monitored gas system of claim 5, further comprising a CPU coupled in signal transmission relationship with the gas sensor to receive said output signal, and wherein the CPU is coupled in controlling relationship to said treating means for at least partial removal of phosgene and/or chlorine dioxide.

7. The monitored gas system of claim 1, wherein the support comprises a porous glass support.

8. The monitored gas system of claim 7, wherein the porous glass support comprises a binderless needled glass mat.

9. The monitored gas system of claim 8, wherein the Ag2O is in the form of a powder dispersed in said binderless needled glass mat.

10. The monitored gas system of claim 1, wherein said gas sensor and filter are disposed in a unitary housing.

11. The monitored gas system of claim 1, wherein the gas sensor comprises an electrochemical sensor.

12. The monitored gas system of claim 11, wherein the electrochemical sensor and filter are disposed in a unitary housing.

13. A gas monitoring system for a source gas, comprising:
 a gas sensor constructed and arranged to detect phosgene in said source gas; and
 a filter for removal of hydrogen sulfide and/or chlorine from the source gas prior to its exposure to the gas sensor, said filter comprising a support impregnated with $Ag_2O$.

14. A method of monitoring a source gas for phosgene and/or chlorine dioxide therein, comprising:
 filtering the source gas to remove hydrogen sulfide and/or chlorine therefrom and produce a filtered source gas, by contacting the source gas with a filter comprising a support having $Ag_2O$ thereon; and
 exposing the filtered source gas to a gas sensor constructed and arranged to detect phosgene and/or chlorine dioxide therein;
 wherein when said source gas contains chlorine dioxide, chlorine is present in said source gas prior to filtering thereof.

15. The method of claim 14, wherein the gas sensor is arranged to provide an output signal correlative of the concentration of phosgene and/or chlorine dioxide therein.

16. The method of claim 15, further comprising treating the source gas subsequent to monitoring thereof by the gas sensor.

17. The method of claim 16, wherein said step of treating the source gas comprises at least partially removing phosgene and/or chlorine dioxide from the source gas.

18. The method of claim 17, wherein said step of at least partially removing phosgene and/or chlorine dioxide is controlled by or in response to the output signal correlative of the concentration of phosgene and/or chlorine dioxide in the source gas.

19. The method of claim 18, further comprising providing a CPU coupled in signal transmission relationship with the gas sensor to receive said output signal, and wherein the CPU is arranged to control the step of at least partially removing phosgene and/or chlorine dioxide.

20. The method of claim 14, wherein the support comprises a porous glass support.

21. The method of claim 20, wherein the porous glass support comprises a binderless needled glass mat.

22. The method of claim 21, wherein the $Ag_2O$ is in the form of a powder dispersed in said binderless needled glass mat.

23. The method of claim 14, wherein said gas sensor and filter are disposed in a unitary housing.

24. The method of claim 14, wherein the gas sensor comprises an electrochemical sensor.

25. The method of claim 24, wherein the electrochemical sensor and filter are disposed in a unitary housing.

* * * * *

UNITED STATES PATENT AND TRADEMARK OFFICE
CERTIFICATE OF CORRECTION

PATENT NO. : 6,840,084 B2
DATED : January 11, 2005
INVENTOR(S) : Nikolskaya Elena It is certified that error appears in the above-identified patent and that said Letters Patent is hereby corrected as shown below:

<u>Column 10,</u>
Line 64, "Ag2O" should be -- $Ag_2O$ --

Signed and Sealed this

Seventeenth Day of May, 2005

JON W. DUDAS
*Director of the United States Patent and Trademark Office*